United States Patent [19]

White et al.

[11] Patent Number: 4,845,374
[45] Date of Patent: Jul. 4, 1989

[54] METHOD AND APPARATUS FOR DETECTING THE DEPOSITION OF AN ADHESIVE ON A TRAVELLING WEB

[75] Inventors: Kenneth W. White, Lewisville; Luis M. Dominguez; Bain C. McConnell, both of Winston-Salem, all of N.C.

[73] Assignee: R. J. Reynolds Tobacco Company, Winston-Salem, N.C.

[21] Appl. No.: 154,775

[22] Filed: Feb. 11, 1988

Related U.S. Application Data

[63] Continuation-in-part of Ser. No. 75,506, Jul. 20, 1987, abandoned.

[51] Int. Cl.[4] ............................................. G01N 21/86
[52] U.S. Cl. ..................................... 250/560; 250/561; 356/448
[58] Field of Search ............... 356/381, 382, 376, 445, 356/446, 448; 250/560, 561

[56] References Cited

U.S. PATENT DOCUMENTS

| | | | |
|---|---|---|---|
| 2,142,052 | 12/1938 | Stephano | 177/311 |
| 2,246,501 | 6/1941 | Bradner et al. | 250/560 |
| 2,773,412 | 12/1956 | Huck | 356/382 |
| 2,797,171 | 6/1957 | Fralish | 117/7 |
| 3,203,547 | 8/1965 | Giulie et al. | 209/111.7 |
| 3,330,961 | 7/1967 | Juengst et al. | 250/219 |
| 3,411,008 | 11/1968 | Coombes et al. | 250/219 |
| 3,819,948 | 6/1974 | Iijima et al. | 250/559 |
| 4,189,335 | 2/1980 | Evans et al. | 156/64 |
| 4,250,382 | 2/1981 | Libby | 250/302 |
| 4,323,772 | 4/1982 | Serge | 235/463 |
| 4,417,934 | 11/1983 | Vaughan | 156/64 |
| 4,525,376 | 6/1985 | Edgerton | 427/10 |

Primary Examiner—David C. Nelms
Attorney, Agent, or Firm—Foley & Lardner, Schwartz, Jeffery, Schwaab, Mack, Blumenthal & Evans

[57] ABSTRACT

A method and apparatus is disclosed that detects the specular reflections from the surface of a travelling web to determine if a material is coated on the web. The web is illuminated with diffuse light and the reflected light is received by a detector which determines the presence and width of the coated material based on the specular reflections from the coated surface of the travelling web.

52 Claims, 2 Drawing Sheets

METHOD AND APPARATUS FOR DETECTING THE DEPOSITION OF AN ADHESIVE ON A TRAVELLING WEB

CROSS REFERENCE TO RELATED APPLICATIONS

This is a continuation-in-part of U.S. application Ser. No. 075,506, filed July 20, 1987 now abandoned.

BACKGROUND OF THE INVENTION

This invention relates to a method and apparatus for detecting the presence of an adhesive on a travelling web. In particular, the invention relates to a method and apparatus that employs specular reflectance to determine the presence of a coating on cigarette tipping paper.

The improper application of adhesive to cigarette tipping paper has been shown to cause severe performance defects in a cigarette. In the cigarette rod can come apart from the filter while the smoker is pulling the cigarette from the pack, in the visual appearance of the product, and insufficient adhesive can impair the performance of the cigarette by changing the draft/dilution characteristics of the cigarette. In the extreme case, insufficient adhesive can cause a burning rod of tobacco to unexpectedly detach from the filter.

All of the aforementioned occurrences are a result of insufficient adhesive being applied to the edge of the tipping paper. For satisfactory adhesion, there must be at least 2 mm of adhesive on the outermost 5 mm of the tipping paper. It would be desirable, therefore, to have a method or device for detecting the presence of the adhesive as well as for quantitatively measuring the width of the adhesive applied to the tipping paper. Such a method or device would have to be capable of inspecting the tipping paper in the cigarette maker at speeds of up to 2.0 meters/second.

Systems have been developed for detecting the presence of he adhesive on a travelling web. U.S. Pat. No. 2,141,052 discloses a system that measures the resistance of the paper as an adhesive is applied. The system disclosed, however, requires undesirable direct contact with the moving web. U.S. Pat. No. 4,417,934 discloses a non-contact system that employs capacitive sensing to detect the presence of the adhesive. While this system avoids direct contact with the web, it is not suited to quantitatively measuring the width of the applied adhesive.

SUMMARY OF THE INVENTION

The object of the presence invention is to provide a method and apparatus for detecting the presence of an adhesive on a travelling web.

Another object of the invention is to provide a method and apparatus for detecting the boundary between two surfaces of a web, one surface being substantially smooth and the other being relatively rough.

Another object of the present invention is to provide a method and apparatus that can detect the width of the adhesive applied to the travelling web.

A still further object of the present invention is to provide an apparatus for detecting the presence of an adhesive on a travelling web having a structure that can easily be employed in a cigarette making machine.

These and other objects are achieved by a method and apparatus that optically enhances the differentiation of the adhesive from the tipping paper by detecting the differences in the specular reflectance of the adhesive and the paper. In a preferred embodiment the invention provides an apparatus comprising:

(a) illumination means for illuminating a surface of said travelling web with diffuse light at a first angle to produce first reflections from a first portion of the surface coated with the coating material and second reflections from a second noncoated portion of the surface;

(b) detector means for receiving at least said second reflections from the surface of said travelling web at a second angle; and (c) processing means for determining the presence of the coating material on the first portion of the surface of said travelling web based on differences in light intensity between the first and second reflections.

Specular or mirror-like reflection occurs when the angle of incidence of the incoming light and the angle of observation of the reflected light are equal or at least approximately the same. With any system of reflected light, there will be a specular component and a diffuse component which together constitute 100% of the reflected light. For shiny or smooth surfaces, e.g., the adhesive area on a paper web, the majority of incident light, as measured at an angle from the normal to the surface of the web, is specularly reflected at an approximately equal angle from the normal. However, when the surface of the object is not smooth, as for example, the nonadhesive area of the paper web, light is scattered at different angles and, therefore, the majority of reflected light is diffuse and the specular component is minimal. This occurs since the microscope contours of the web surface which are responsible for reflectance of the light are not necessarily aligned parallel to the overall web surface.

For diffuse light sources, the incident light on any given point of the web emanates from a number of point sources, and thus the angle of incidence must be considered as a range of angles from the web reflectance point to the plural point sources. When a relatively rough surface such as the non-adhesive areas on the paper web are illuminated by a single point light source or by a light source having a relatively narrow range of angles of incident light, substantial amounts of reflected light can be observed at most angles of observation relative to the normal from the web surface, regardless of the angle or angles of incidence. On the other hand, with relatively smooth or substantially mirror-like surfaces and, when illuminated in the same manner, i.e., with a relatively narrow range of angles of incident light, the majority of light is specularly reflected at the same narrow range of angles measured with respect to the normal of the paper surface. Therefore, with this smooth surface, the amount of reflected light which can be observed will be small at most angles of observation (angles of observation which are different than the angles of illumination). Thus, when one observes incident light reflected from the surfaces of the smooth adhesive and the rough web, the optical gain, i.e., intensity of reflected light, of the adhesive is substantially different than the optical gain of the web or tipping paper. Specifically, when the source of illumination is a point source or a diffuse source providing a relatively narrow range of angles of incident light, if the reflected light is viewed at an angle of observation equal to, or within the range of, the angle of illumination, the optical gain from the smooth adhesive surface will be substantially higher than that of the rough web surface. On the other hand, with the same source of illumination, if the angle of observation is substantially different than the angle or angles of illumination, the optical gain of the smooth adhesive surface will be substantially lower than the optical gain of the rough web surface.

Because of these differences in intensity of reflected light from the rough (web) and smooth (adhesive) surfaces, the invention can be employed for the purposes of differentiating between adhesive and paper surfaces at substantially any combination of illumination and observation angles between 0° and the limit of 90°. Advantageously, the angle of incidence of the incoming light and the angle of observation of reflected light are selected to be equal and to be between approximately 45° and 90° from the axis normal to the tipping paper. In this instance, the light reflected from the adhesive will be of higher intensity than the light reflected from the rough web and thus, the adhesive will appear bright and the web dark (relative to the adhesive). In the preferred embodiment described herein, the differences between the adhesive and the paper are most readily apparent if the angle of incidence of the incoming light and the angle of observation of the reflected light are equal with respect to the surface normal and are limited to between about 70° and about 90°.

Alternatively, in another advantageous embodiment, it is possible to take advantage of the relatively constant (over substantially any angle of observation between 0° and 90°) intensity of diffuse reflection of the paper surface and to employ the combination of angles of incident light and angles of observation which are outside the specular combinations for the adhesive surface; such as the combination of a small angle of incidence, e.g., between 0° and 20°, with a relatively large angle of observation, e.g., between 70° and 90°; or vice versa, i.e., large angles of incidence and small angles of observation. In this instance, the paper appears white or bright and the adhesive appears dark (relatively) since observation of light reflected from the adhesive surface is minimized.

The invention provides significant advantages over prior art devices in detecting both the presence and width of one or more lines of adhesive on tipping paper.

BRIEF DESCRIPTION OF THE DRAWINGS

With the above as background, reference should now be made to the following figures for a detailed description of the invention.

DETAILED DESCRIPTION OF THE PREFERRED EMBODIMENTS

Figure 1:
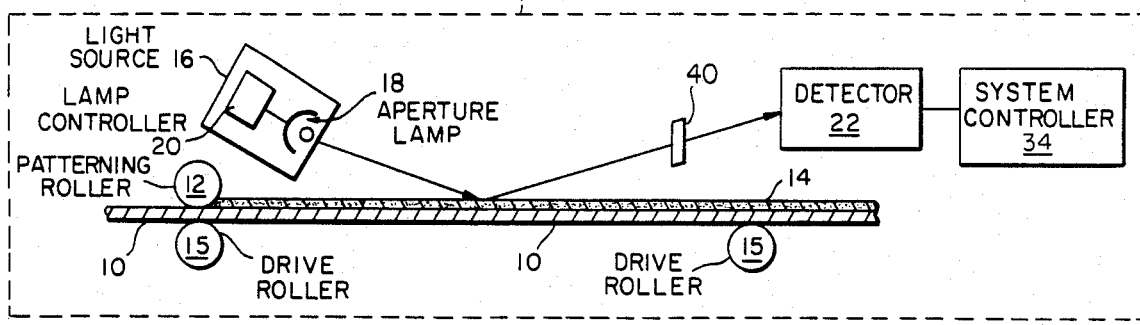
FIG. 1 is a block diagram of a cigarette manufacturing machine incorporating the present invention.

A cigarette manufacturing machine 8 is shown in FIG. 1, wherein a web of tipping paper 10 for use in cigarettes is drawn past a patterning roller 12 that applies an adhesive layer 14 to the surface of the tipping paper 10. As the tipping paper 10 is drawn along the transport path by drive rollers 15, the surface of the paper 10 is illuminated by a light source 16. The light source 16 is comprised of a fluorescent aperture lamp 18 that provides diffused and spectrally stable light. A lamp controller 20 is provided to regulate the output of the lamp 18 and prevent ripple. The lamp controller 20 also overdrives the fluorescent aperture lamp 18 in order to obtain sufficient illumination for the detector 22. The lamp controller 20 and fluorescent aperture lamp are readily available components. (For example, MERCRON of Richardson, Tex. is one company that produces lamp controllers for fluorescent aperture lamps suitable for use in the present invention).

Figure 2:
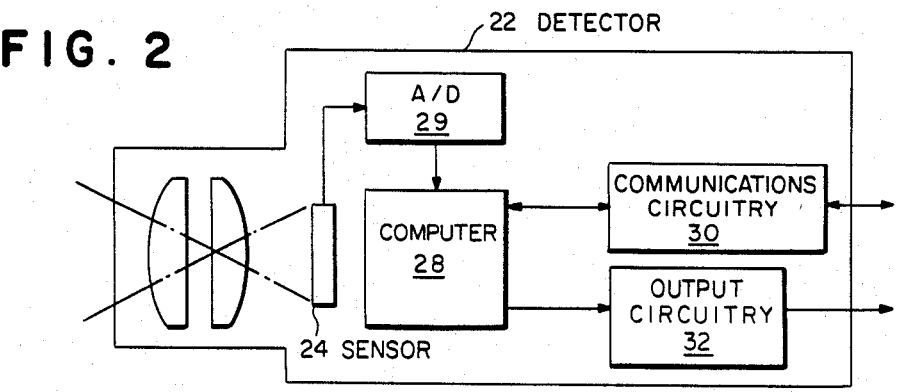
FIG. 2 is a schematic block diagram of a detector employed in the present invention.

In a preferred embodiment, the detector 22 is a Honeywell HVS 256 High Accuracy Edge/Width Gauge detector. The HVS 256 detector is capable of performing high speed, non-contact, on-line inspection and gauging. As shown in FIG. 2, the HVS 256 detector has a CCD line scan sensor 24 having 256 pixels, an onboard computer 28, an A/D converter 29, and associated communications circuitry 30 and output circuitry 32. The HVS 256 detector can be programmed to detect up to eighteen edge positions and widths or centers (differences or midpoints between any two edges) along the pixel array that are calculated by the computer 28 and output in state, analog, or digital format. Typically, the HVS 256 detector is employed to measure parts that are placed in an object plane. The difference in reflectance between the background of the object plane and the part is detected as an edge transition. In other words, variations in surface reflectance produce brightness variations giving contrast (grey levels) which are converted to an electrical signal by the CCD line scan sensor 24, and transitions in the electrical signal are detected as the edges of the object by edge detection algorithms within the microprocessor of the HVS 256 detector. In the present invention, the HVS 256 detects the difference in the specular reflectance of the adhesive layer 14 and any uncoated areas of the tipping paper 10. The output of the detector 22 is supplied to a system controller 34 (FIG. 1) that controls the overall operation of the cigarette making machine 8.

Figure 3:
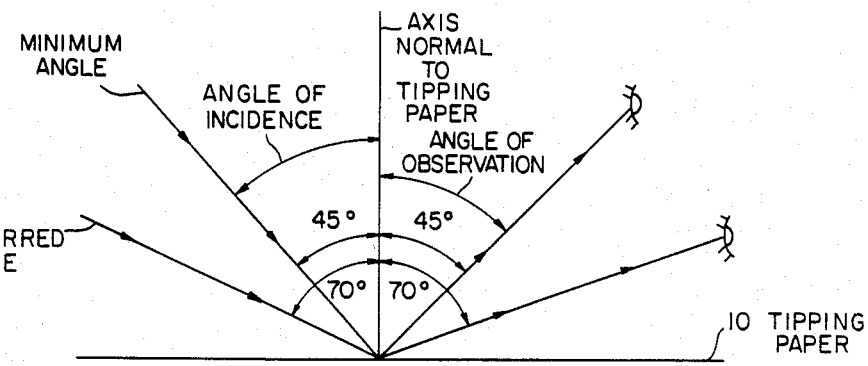
FIG. 3 is a diagram illustrating the angle of incidence of illuminated light and the angle of observation of specular reflections employed in the present invention.
Figure 4A:
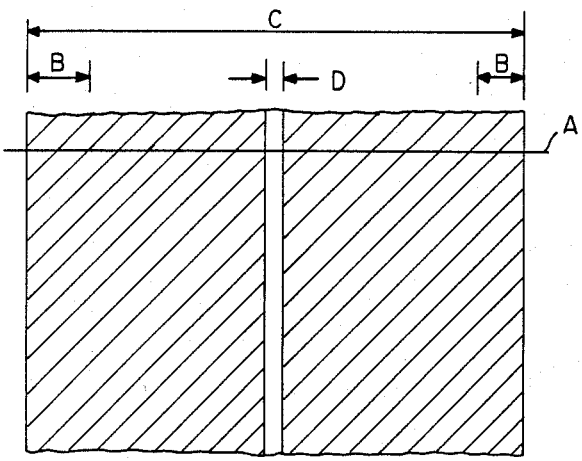
FIGS. 4a, 5a and 6a represent typical adhesive patterns detected by the present invention.
Figure 4B:
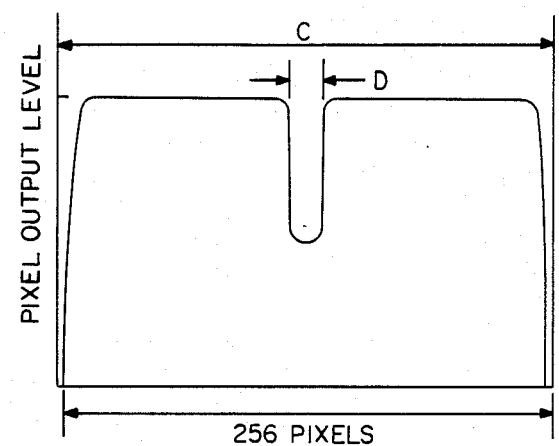
FIGS. 4b, 5b and 6b represent the output signal from a CCD line scanner for the detector shown in FIG. 2 when viewing the adhesive patterns shown in FIGS. 4a–6a respectively.
Figure 5A:
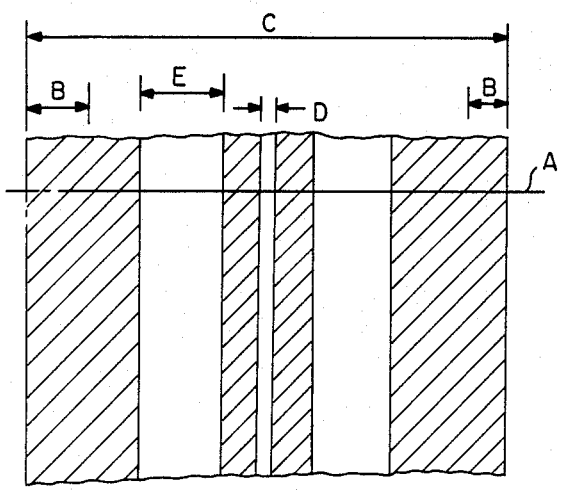
Figure 5B:
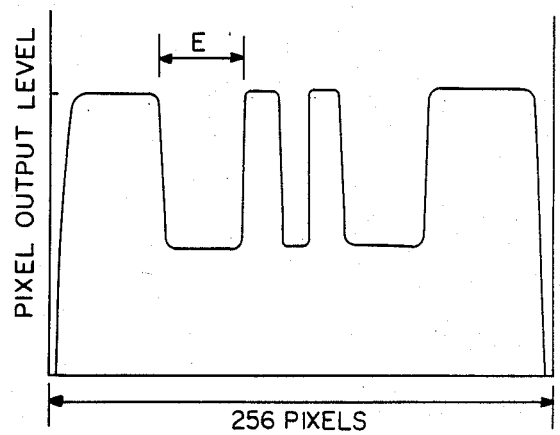
Figure 6A:
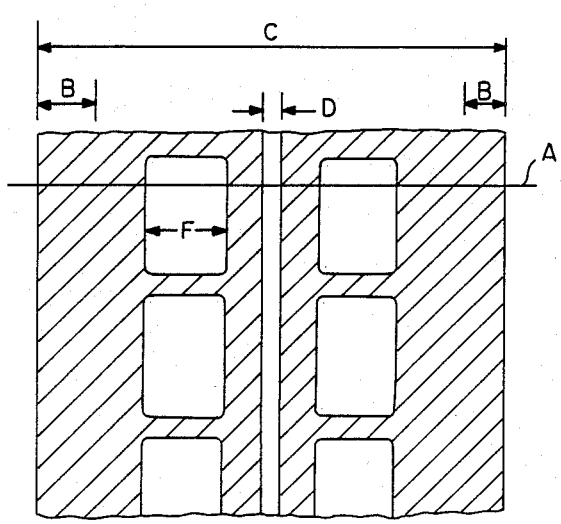
Figure 6B:
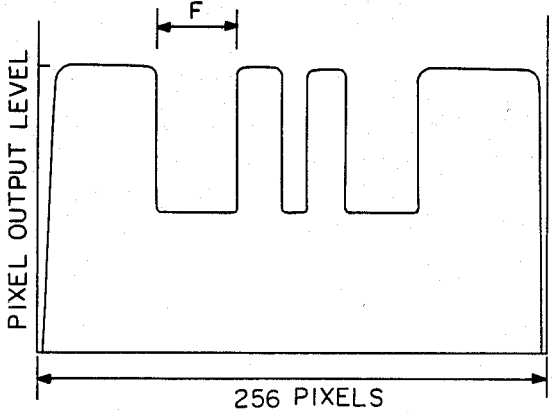

The illumination source 16 and the detector 22 are positioned in order to enhance the differences in the specular reflectance of uncoated areas of the tipping paper 10 and the adhesive layer 14 which has been applied to the paper. The angle of incidence for the illumination light and the angle of detection are preferably equal and selected to be between about 45° and 90° from an axis normal to the surface of the tipping paper 10 in order to optimize the ratio of intensity of observed specularly reflected light (from the adhesive surface) to the diffuse reflected light (from the web surface, e.g., see FIG. 3). Most preferably, the angle of incidence and the angle of detection are between 70° and 90° in order to achieve the best results. At the prescribed angles, the adhesive layer 14 reflects diffuse light in a mirrorlike manner that makes the adhesive layer 14 readily ascertainable from the surface of the tipping paper 10. Thus, the adhesive layer appears bright and the paper dark. It is essential that the illumination source 16 provide a uniform diffuse light in the across-machine direction, e.g., horizontally in FIG. 4, in order to prevent any bright or "hot" spots that might be generated from non-uniform point source dispersement of the light. A wide diffuse light source also reduces the criticality of the side to side alignment of the detector 22 and improves the accuracy of edge detection.

In other embodiments of the invention the angle of incidence is selected to be less than 45° and preferably between 0° and 20° with a relatively large angle of observation of between 70° and 90°. More generally, the angle of incidence may range from 0°–40° with the angle of observation between 50°–90°. In both of these cases, the adhesive layer appears darker with the paper being brighter. In yet another embodiment, the angle of incidence may be large, on the order of 70°–90° (or more generally 50°–90°) with the angle of observation between 0°–20° (or more generally 0°–40°). In these latter cases as well, the paper appears brighter than the adhesive layer reflections. In other words, the adhesive layer appears darker than the paper since the angle of observation is substantially outside the range where one can observe the specularly reflected light from the adhesive layer.

In a specific example of the embodiment described immediately above, the web may be illuminated at an angle of incidence with a diffuse light source to produce first and second reflections. The first reflections are from a first portion of the surface of the web which is coated with the coating material, e.g., glue. These first reflections may be observed as specular reflections with light intensity $I_1$, if the observation angle is substantially equal to the angle of incidence. These first reflections may also be observed with a light intensity $I_2$ less than $I_1$ if observed as non-specular reflections, namely, at angles not substantially equal to the incidence angle. The second reflections from the web come from a second portion of the web which is not coated. These reflections are largely diffuse reflections (insignificant specular component) and have a minimum to maximum range of intensities $I_{3\ min}$–$I_{3\ max}$ all of which are intermediate between $I_1$ and $I_2$, for the range of all angles of observation (0°–90°). Thus, by knowing in advance, e.g., by empirical testing, the expected intensities $I_1$, $I_2$, $I_{3\ min}$ and $I_{3\ max}$ it is possible to determine the existence of the coated material on the web by observing the reflected light at virtually any angle (0°–90°) and by using incident light at virtually any angle (i.e., between 0°–90°). In all cases, $I_2 < I_3 < I_1$ where $I_3$ represents any value between the minimum and maximum values, $I_{3\ min}$ and $I_{3\ max}$, respectively. Thus, if the received light has an intensity only varying between $I_{3\ min}$–$I_{3\ max}$, no coating is contained on the web. On the other hand, if the received light intensity is higher ($I_1$) or lower ($I_2$) during part of the scan, then that part of the scan corresponds to the coated portion of the web.

In one advantageous embodiment of the invention, the ratio of intensities of reflected light from the adhesive to reflected light from the web can be further enhanced by employing a polarizing filter between the web surface and the detector as shown by filter 40 in FIG. 1. If the angles of illumination and observation are in a range near Brewster's Angle, i.e., 56.71° from the normal, the smooth adhesive tends to polarize the reflected light horizontally. Some small degree of polarization occurs in the light reflected from the web, but this will be substantially less than with the light reflected from adhesive. By detecting through polarizing filter 14 aligned to preferentially pass the horizontally polarized light, the intensity of light reflected from the adhesive is only minimally reduced; however, since the rough surfaces does not tend to promote significant polarization, the intensity of reflected light from the web surface is reduced nearly in half by the blocking action of the polarizing filter. As a result, contrast between the smooth adhesive and the rough filter web is increased substantially.

The detector 22 detects the differences in the specular reflections from the adhesive layer 14 and any uncoated areas of the tipping paper 10, finds the edges, and then calculates the width of the adhesive layer 14. If the adhesive layer 14 is not present or out of a specified width range, the detector 22 provides an output signal to the system controller 34 indicating the out of range condition. The system controller 34 notes the location of the defect in the tipping paper 10 in memory and causes the rejection of cigarettes made from the defective tipping paper 10 at a downstream location of the cigarette manufacturing machine 8. For example, given known parameters such as the distance (in filter tipping paper cigarette units) from the detector 22 to a rejection station (not shown) the system controller 34 notes the position $X_O$ of the detection of an out of range condition and is programmed to reject the cigarettes made from the defective tipping paper 10 when they pass the rejection station at $X_1$ positional units later. The operation of a system controller 34 to control a cigarette manufacturing machine 8 is well known within the cigarette manufacturing industry.

Examples of typical adhesive patterns detected by the present invention are shown in FIGS. 4a–6a and the associated output signal from the CCD line scanner 24 are shown in FIGS. 4b–6b. The signal output shown in FIGS. 4b–6b represent the output of the CCD line scanner 24 when it scans the tipping paper 10 along line A shown in FIGS. 4a–6a. The shaded areas of FIGS. 4a–6a represent the adhesive layer 14 applied to the surface of the tipping paper 10. In all three cases the adhesive layer extends to the edge of the tipping paper 10. The areas B along the edge of the paper 10 are the most critical areas requiring the presence of adhesive. Preferably there is at least a 2 mm wide strip of adhesive within the 5 mm wide areas B.

The Honeywell HVS 256 detector employed for the detector 22 can be programmed to "learn" what is considered a minimum condition by using Boolean logic to make decisions. For example, a sample tipping paper lacking adhesive in a 3 mm wide strip along the edge of the tipping paper is first placed in front of the detector 22. A switch is then activated causing the detector 22 to "remember" the limit, i.e., the signal pattern generated by the CCD line scanner 24 when viewing the sample tipping paper is stored by the computer 28. Alternately, the threshold values for determining the adhesive/paper boundary may be input into computer 28. In operation, the computer 28 continuously compares the signal generated from the CCD line scanner 24 with the remembered signal pattern. If an edge transition is not detected within the first 3 mm of the edge of the tipping paper, an out of range signal is generated.

The Honeywell HVS 256 detector utilized for detector 22 can also determine the distance between edge transitions. Thus, the overall width C of the adhesive layer can be determined, or the width of any intermediate areas where adhesive is not applied can be ascertained. The width of area D is of interest. The width of the tipping paper 10 shown in FIGS. 4a–6a is used for two cigarettes during the manufacturing process. The tipping paper 10 is cut along the length of area D and it is therefore desirable that adhesive not be present in this area. The width of area D should preferably be maintained at about 1 mm. Other non-adhesive areas (for example, areas E and F shown in FIGS. 5a and 6a) that are perforated may be provided to regulate air flow in the cigarette filter. In such cases, it would also be desirable to monitor the width of the nonadhesive areas to determine if they are also within specified ranges. Additionally, trends can be monitored by the system controller 34 by receiving the width information directly from the detector 22 so that problems may be detected before an actual out of range condition is generated.

Figure 7:
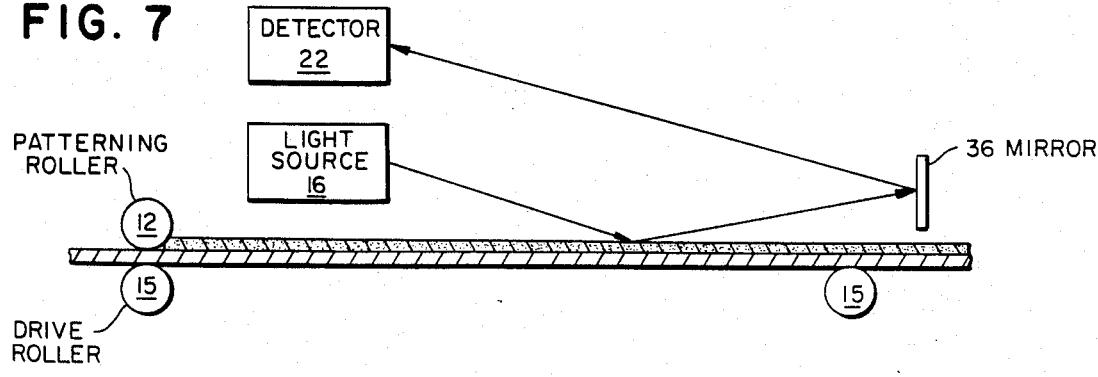
FIG. 7 illustrates a second embodiment of the present invention.

Due to the nature of the cigarette manufacturing machine 7, it may not be possible to physically locate the detector 22 at the correct angle of observation due to space restrictions. In such situations, a folded optics arrangement as shown in FIG. 7 may be employed. A mirror 36 is positioned at the appropriate angle of observation to provide the image from the adhesive layer 14 and tipping paper 10 to the detector 22.

The detection of the specular reflections from the adhesive layer 14 and the tipping paper 10 permits accurate determination of the presence and width of the adhesive layer 14 not previously achieved in prior art devices. The diffuse light source employed in the present invention enhances the uniformity of specular reflections from the adhesive layer 14 and the tipping paper 10, allowing for easy detection of the edge transitions between the adhesive layer 14 and the surface of the tipping paper 10 by the detector 22.

The invention has been described in detail with particular reference to preferred embodiments thereof, but it will be understood that variations and modifications can be effected within the spirit and scope of the invention. For example, a 256×256 array scanner may be employed with a separate microprocessor performing the edge detection algorithms. In this case a single line of the array is utilized for data analysis.

What is claimed is:

1. An apparatus for measuring the width of a portion of a travelling web, said apparatus comprising:
    (a) illumination means for uniformly illuminating a transverse surface of said travelling web with diffuse light at a first angle to produce first reflections from a first portion of said surface coated with a coating material and second reflections from a second, non-coated portion of said surface, said first and second portions being transverse to the direction of travel of said web;
    (b) detector means positioned at a second angle for receiving said first and second reflections from the surface of said travelling web, and for producing signals indicative of the intensities of said first and second reflections as a function of the transverse distance across said web; and
    (c) processing means connected to said detector means for receiving said signals and for determining the width of at least one of said first portion or said second portion of said surface of said travelling web based on differences in light intensity between said first and second reflections.

2. An apparatus as claimed in claim 1, further comprising means for directing said first reflections to said detector means.

3. An apparatus as claimed in claim 1, wherein said first and second angles are approximately equal such that said first reflections include a predominantly specular component and said first and second angles are each about 45° to 90° from an axis normal to said travelling web.

4. An apparatus as claimed in claim 3, wherein said first and second angles are at least approximately equal and about 70° to 90° from an axis normal to said travelling web.

5. An apparatus as claimed in claim 1, wherein said first angle is less than 45° and said second angle is between 70°-90°.

6. An apparatus as claimed in claim 1, wherein said first angle is between 0°-20° and said second angle is between 70°-90°.

7. An apparatus as claimed in claim 1, wherein said first angle is between 0°-40° and said second angle is between 50°-90°.

8. An apparatus as claimed in claim 1, wherein said first angle is between 50°-90° and said 9. An apparatus as claimed in claim 1, wherein said first angle is between 70°-90° and said second angle is between 0°-20°.

10. An apparatus as claimed in claim 1, further including a polarizing filter disposed between said web and said detector.

11. An apparatus as claimed in claim 10, wherein said first and second angles are each approximately equal to Brewster's angle.

12. A method of measuring the width of a portion of a surface of a travelling web, said method comprising the steps of:
    (a) uniformly illuminating said surface of said travelling web with diffuse light at a first angle to produce first reflections from a first portion of said surface coated with said coating material and second reflections from a second, non-coated portion of said surface, said first and second portions being transverse to the direction of transverse of said web;
    (b) receiving at a second angle said first and second reflections from the surface of said travelling web;
    (c) generating signals indicative of the intensities of said first and second reflections as a function of the transverse distance across said web; and
    (d) determining the width of at least one of said first and second portions based on differences in light intensity between said first and second reflections.

13. A method of detecting the presence of a coating material on a surface of a travelling web as claimed in claim 12, wherein said first and second angles are at least approximately equal and are about 45° to 90° from an axis normal to said travelling web.

14. A method of detecting the presence of a coating material on a surface of a travelling web as claimed in claim 13, wherein said first and second angles are at least approximately equal and are about 70° to 90° from an axis normal to said travelling web.

15. A method as claimed in claim 12, wherein said first angle is less than 45° and said second angle is between 70°-90°.

16. A method as claimed in claim 12, wherein said first angle is between 0°-20° and said second angle is between 70°-90°.

17. A method as claimed in claim 12, wherein said first angle is between 0°-40° and said second angle is between 50°-90°.

18. A method as claimed in claim 12, wherein said first angle is between 50°-90° and said second angle is between 0°-40°.

19. A method as claimed in claim 12, wherein said first angle is between 70°-90° and said second angle is between 0°-20°.

20. An apparatus for measuring the width of a travelling web, said apparatus comprising:
   (a) illumination means for uniformly illuminating a surface of said web with diffuse light at a first angle to produce first reflections from a first portion of said surface having a relatively smooth material thereon and second reflections from a second portion of said surface not having said relatively smooth material thereon, said first and second portions being transverse to the direction of travel of said web;
   (b) detector means positioned at a second angle for receiving said first and second reflections from the surface of said web, and for producing signals indicative of the intensities of said first and second reflections as a function of the transverse distance across said web; and
   (c) processing means connected to said detector means for receiving said signals and for determining the width of at least one of said first portion or said second portion of said surface of said web based on differences in light intensity between said first and second reflections.

21. A method of measuring the width of a portion of a surface of a travelling web, said method comprising the steps of:
   (a) uniformly illuminating said surface of said web with diffuse light at a first angle to produce first reflections from a first portion of said surface having a relatively smooth material thereon and second reflections from a second portion of said surface not having said relatively smooth material thereon, said first and second portions being transverse to the direction of travel of said web;
   (b) receiving said first and second reflections from the surface of said web at a second angle;
   (c) generating signals indicative of the intensities of said first and second reflections as a function of the transverse distance across said web; and
   (d) determining the width of at least one of the first and second portions based on the differences in light intensity between said first and second reflections.

22. A method of measuring the width of a portion of a travelling web comprising the steps of:
   (a) illuminating, at an angle of incidence, said surface of said travelling web with a diffuse light source to produce first reflections from a first portion of said surface coated with said coating material and second reflections from a second portion of said surface not coated with said coating material, said first reflections having a first light intensity when observed at an angle of observation substantially equal to said angle of incidence, and a second intensity when observed at an angle of observation not substantially equal to said angle of incidence, said second reflections having a range of third light intensities intermediate said first and second light intensities, said first and second portions being transverse to the direction of transverse of said web;
   (b) positioning a light detector at an angle of observation for receiving said first and second reflections;
   (c) generating signals indicative of the intensities of said first and second reflections as a function of the transverse distance across said web; and
   (d) responsive to said signals, automatically determining the width of at least one of said first and second portions based on the difference in light intensities between at least two of said first, second and third intensities.

23. A method as recited in claim 22, further comprising the step of determining the width of said first portion.

24. A method as recited in claim 23, wherein said angle of incidence is between about 70° to 90° as measured from an axis normal to said travelling web.

25. A method as recited in claim 23, wherein said angle of incidence is between about 45° to 90° as measured from axis normal to said travelling web.

26. A method as recited in claim 22, wherein said angle of incidence is less than 45° and said angle of observation is between 70°-90°.

27. A method as recited in claim 22, wherein said angle of incidence is between 0°-20° and said angle of observation is between 70°-90°.

28. A method as recited in claim 22, wherein said angle of incidence is between 0°-40° and said angle of observation is between 50°-90°.

29. A method as recited in claim 22, wherein said angle of incidence is between 50°-90° and said angle of observation is between 0°-40°.

30. A method as recited in claim 22, wherein said angle of incidence is between 70°-90° and said angle of observation is between 0°-20°.

31. Apparatus for measuring the width of a portion of a surface of a travelling web comprising:
   (a) means for illuminating, at an angle of incidence, said surface of said travelling web with a diffuse light source to produce first reflections from a first portion of said surface coated with said coating material and second reflections from a second portion of said surface not coated with said coating material, said first reflections having a first light intensity when observed at an angle of observation substantially equal to said angle of incidence, and a second intensity when observed at an angle of observation not substantially equal to said angle of incidence, said second reflections having a range of third light intensities intermediate said first and second light intensities, said first and second portions being transverse to the direction of travel of said web;
   (b) light detector means for receiving, at an angle of observation, said first and second reflections, and for producing signals indicative of the intensities of said first and second reflections as a function of the transverse distance across said web;
   (c) means responsive to said signals for automatically determining the width of at least one of said first and second portions based on the differences in light intensity between at least two of said first, second and third intensities.

32. Apparatus for detecting the presence of a coating material on a travelling web comprising:
   (a) illumination means for uniformly illuminating a surface of said travelling web with diffuse light at a first angle;
   (b) said web having a first portion of said surface having said coating material thereon and a second, discrete portion not having said coating material thereon;

(c) said illumination means producing first reflections from said first, coated portion of said web and second reflections from said second, non-coated portion of said web;

(d) detector means positioned at a second angle for receiving said first and second reflections from the surface of said travelling web; and (e) processing means, connected to said detector means, for separately determining the light intensity of said first and second reflections and for detecting the presence of said coating material on said first portion of said travelling web based on differences in light intensity between said first and second reflections.

33. An apparatus as claimed in claim 32, wherein said processing means determines the width of said coating material based on the first reflections received by said detector means.

34. An apparatus as claimed in claim 32, further comprising means for directing said first reflections to said detector means.

35. An apparatus in claim 32, wherein said first and second angles are approximately equal such that said first reflections include a predominantly specular component and said first and second angles are each about 45° to 90° from an axis normal to said travelling web.

36. An apparatus as claimed in claim 35, wherein said first and second angles are at least approximately equal and about 70° to 90° from an axis normal to said travelling web.

37. An apparatus as claimed in claim 32, wherein said first angle is less than 45° and said second angle is between 70°-90°.

38. An apparatus as claimed in claim 32, wherein said first angle is between 0°-20° and said second angle is between 70°-90°.

39. An apparatus as claimed in claim 32, wherein said first angle is between 0°-40° and said second angle is between 50°-90°.

40. An apparatus as claimed in claim 32, wherein said first angle is between 50°-90° and said second angle is between 0°-40°.

41. An apparatus as claimed in claim 32, wherein said first angle is between 70°-90° and said second angle is between 0°-20°.

42. An apparatus as claimed in claim 32, further including a polarizing filter disposed between said web and said detector.

43. An apparatus as claimed in claim 42, wherein said first and second angles are each approximately equal to Brewster's angle.

44. A method of detecting the presence of a coating material on a surface of a travelling web, said method comprising the steps of:

(a) uniformly illuminating said surface of said travelling web with a diffuse light source at a first angle;

(b) providing said web with a first portion of said surface having said coating material thereon and a second, discrete portion not having said coating material thereon;

(c) orienting said web and said diffuse light source for producing first reflections from said first portion of said web coated with said coating material and second reflections from said second, non-coated portion of said web;

(d) receiving at a second angle said first and second reflections from the surface of said travelling web;

(e) separately determining the light intensities of said first and second reflections; and (f) detecting the presence of said coating material on the first portion of said travelling web based on differences in light intensity between said first and second reflections.

45. A method of detecting the presence of a coating material on a surface of a travelling web as claimed in claim 44, further comprising the step of determining the width of said, coating material based on the first reflections.

46. A method of detecting the presence of a coating material on a surface of a travelling web as claimed in claim 44, wherein said first and second angles are at least approximately equal and are about 45° to 90° from an axis normal to said travelling web.

47. A method of detecting the presence of a coating material on a surface of a travelling web as claimed in claim 46, wherein said first and second angles are at least approximately equal and are about 70° to 90° from an axis normal to said travelling web.

48. A method as claimed in claim 44, wherein said first angle is less than 45° and said second angle is between 70°-90°.

49. A method as claimed in claim 44, wherein said first angle is between 0°-20° and said second angle is between 70°-90°.

50. A method as claimed in claim 44, wherein said first angle is between 0°-40° and said second angle is between 50°-90°.

51. A method as claimed in claim 44, wherein said first angle is between 50°-90° and said second angle is between 0°-40°.

52. A method as claimed in claim 44, wherein said first angle is between 70°-90° and said second angle is between 0°-20°.

* * * * *

UNITED STATES PATENT AND TRADEMARK OFFICE
CERTIFICATE OF CORRECTION

PATENT NO. : 4,845,374

DATED : July 4, 1989

INVENTOR(S) : Kenneth W. White et al.

It is certified that error appears in the above—identified patent and that said Letters Patent is hereby corrected as shown below:

Col. 1, line 20 after "In" (second occurrence) insert --the least alarming aspects of its manifestations,--.

Col. 1, line 22 after "pack," insert --the fold-over of the tipping paper can cause defects--.

Col. 8, line 17 after "said" insert --second angle is between 0° - 40°.--

Signed and Sealed this

Tenth Day of April, 1990

*Attest:*

HARRY F. MANBECK, JR.

*Attesting Officer*      *Commissioner of Patents and Trademarks*